United States Patent
Norris et al.

(10) Patent No.: US 6,476,040 B1
(45) Date of Patent: Nov. 5, 2002

(54) PROCESSES AND INTERMEDIATES FOR PREPARING ANTI-CANCER COMPOUNDS

(75) Inventors: Timothy Norris, Gales Ferry; Dinos P. Santafianos, Groton; Richard S. Lehner, Ledyard, all of CT (US)

(73) Assignees: Pfizer Inc., New York, NY (US); Pfizer Products Inc., Groton, CT (US)

(*) Notice: Subject to any disclaimer, the term of this patent is extended or adjusted under 35 U.S.C. 154(b) by 0 days.

(21) Appl. No.: 09/538,635

(22) Filed: Mar. 30, 2000

Related U.S. Application Data

(60) Provisional application No. 60/127,072, filed on Mar. 31, 1999.

(51) Int. Cl.[7] .................... A01N 43/54; A61K 31/505; C07D 239/72
(52) U.S. Cl. .................... 514/259; 544/283; 544/293
(58) Field of Search .................... 514/259; 544/283, 544/293

(56) References Cited

U.S. PATENT DOCUMENTS 5,747,498 A 5/1998 Schnur et al. ............... 514/259

FOREIGN PATENT DOCUMENTS

| EP | 0566226 | 10/1993 |
| NZ | 245662 | 9/1995 |
| WO | 9730035 | 8/1997 |
| WO | 9732856 | 9/1997 |
| WO | 9813354 | 4/1998 |
| WO | WO 99/03803 | 1/1999 |
| WO | WO 99/55683 | 11/1999 |

Primary Examiner—Mukund J. Shah
Assistant Examiner—Tamthom N. Truong
(74) Attorney, Agent, or Firm—Ladas & Parry

(57) ABSTRACT

The present invention relates to methods and intermediates for preparing compounds of the formula 1

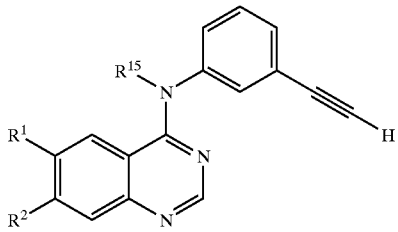

and the pharmaceutically acceptable salts and solvates thereof, as well as structurally related compounds, wherein $R^1$, $R^2$ and $R^{15}$ are as defined herein. The foregoing compounds are useful in the treatment of hyperproliferative disorders, such as cancers, in mammals.

17 Claims, No Drawings

PROCESSES AND INTERMEDIATES FOR PREPARING ANTI-CANCER COMPOUNDS

This application claims the benefit of U.S. Provisional Application No.: 60/127,072, filed Mar. 31, 1999.

BACKGROUND OF THE INVENTION

The present invention relates to processes and intermediates for preparing compounds that are useful in the treatment of hyperproliferative disorders, such as cancers, in mammals.

U.S. Pat. No. 5,747,498, which issued on May 5, 1998 and is incorporated herein by reference in its entirety, refers to a novel series of quinazoline derivatives, including [6,7-bis(2-methoxyethoxy)-quinazolin-4-yl]-(3-ethynylphenyl) amine hydrochloride, which are inhibitors of the erbB family of oncogenic and protooncogenic protein tyrosine kinases, such as epidermal growth factor receptor (EGFR), and are therefore useful for the treatment of proliferative disorders, such as cancers, in humans. United States provisional patent application 60/083,441 entitled "N-(3-ethynylphenylamino)-6,7-bis(2-methoxyethoxy)-4-quinazolinamine Mesylate Anhydrate And Monohydrate," filed Apr. 29, 1998, with named inventors T. Norris, D. Santafianos, D. J. M. Allen, R. M. Shanker, and J. W. Raggon, which is incorporated herein by reference in its entirety, refers to N-(3-ethynylphenylamino)-6,7-bis(2-methoxyethoxy)-4-quinazolinamine mesylate anhydrate and hydrate forms which possess the same anti-cancer utility as the corresponding hydrochloride salt referred to above. The present invention relates to methods and intermediates for preparing anti-cancer compounds referred to in the United States patent and patent application referred to above.

SUMMARY OF THE INVENTION

The present invention relates to a process for preparing compounds of the formula

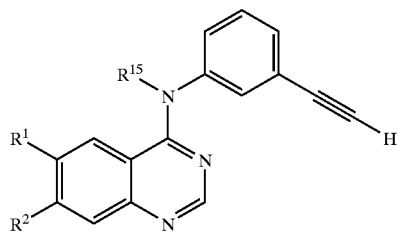

and pharmaceutically acceptable salts and solvates of said compounds, wherein:

$R^1$ and $R^2$ are each independently selected from $C_1$–$C_{10}$ alkyl and $C_1$–$C_{10}$ alkoxy wherein said alkyl and alkoxy are optionally substituted by up to 2 substituents independently selected from hydroxy and $C_1$–$C_6$ alkoxy;

$R^{15}$ is H, $C_1$–$C_{10}$ alkyl, or —$(CH_2)_q(C_6$–$C_{10}$ aryl), wherein q is an integer from 0 to 4;

which comprises treating a compound of the formula 2

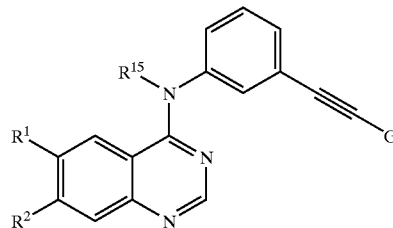

wherein $R^{15}$, $R^1$ and $R^2$ are as defined above, and G is a blocking group from —$C(OH)R^3R^4$ and —$SiR^3R^4R^5$; with either (a) an alkali-metal or alkaline-metal hydroxide in a solvent comprising a hydroxy-substituted $C_1$–$C_{10}$ alkyl where G is —$C(OH)R^3R^4$, or (b) a tetra-$(C_1$–$C_6$ alkyl)-ammonium fluoride compound in an aprotic solvent where G is —$SiR^3R^4R^5$.

In a preferred embodiment, where G is —$C(OH)R^3R^4$, said solvent is a secondary alcohol, such as butan-2-ol or isopropanol, and said alkali-metal or alkaline-metal hydroxide is selected from sodium hydroxide, lithium hydroxide, cesium hydroxide, calcium hydroxide, magnesium hydroxide and potassium hydroxide, most preferably sodium hydroxide.

In another preferred embodiment, where G is —$SiR^3R^4R^5$, said tetra-$(C_1$–$C_6$ alkyl)-ammonium fluoride compound is tetra-(n-butyl)-ammonium fluoride and said aprotic solvent solvent is selected from tetrahydrofuran (THF), diethyl ether, dimethoxyethane (DME), toluene, dichloromethane, chloroform, and mixtures of two or more of the foregoing solvents, most prefereably THF.

The present invention also relates to the preparation of a compound of formula 2, as described above, which comprises treating a compound of the formula 3

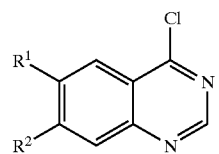

wherein $R^1$ and $R^2$ are as defined above, with a compound of the formula 4

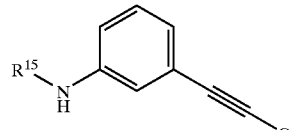

wherein G and $R^{15}$ are as defined for said compound of formula 2.

In a preferred embodiment of the above method, the compound of formula 3 is treated with the compound of formula 4 in an organic solvent such as dimethylformamide (DMF), dimethylsulfoxide (DMSO), THF, acetonitrile (MeCN), or a mixture of two or more of the foregoing solvents, more preferably acetonitrile.

The present invention also relates to the preparation of the compound of formula 3, as defined above, which comprises treating a compound of formula 5

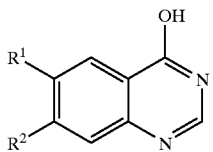

with thionyl chloride in anhydrous dichloromethane.

In a preferred embodiment of each of the reactions described above, $R^1$ and $R^2$ are both 2-methoxyethoxy and $R^{15}$ is H.

The present invention also relates to the preparation of compounds of the formula 6 and 7

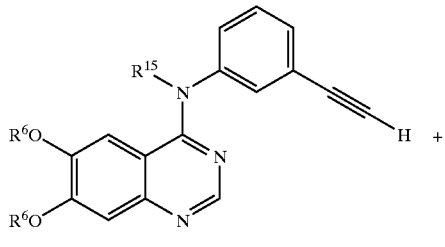

6

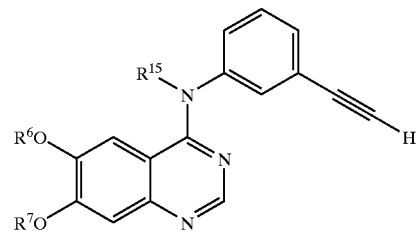

7 and the pharmaceutically acceptable salts and solvates thereof, wherein $R^{15}$ is as defined above, $R^6$ is $C_1-C_{10}$ alkyl or $-(CH_2)_mO(CH_2)_nCH_3$;

$R^7$ is $C_1-C_{10}$ alkyl or $-(C_1-C_6$ alkyl$)(C_6-C_{10}$ aryl$)$ wherein the foregoing $R^7$ groups are optionally substituted by 1 to 3 substituents independently selected from halo, nitro, trifluoromethyl, trifluoromethoxy, $(C_1-C_6$ alkyl$)$sulfonyl, $C_1-C_6$ alkyl, $C_1-C_6$ alkoxy, $C_6-C_{10}$ aryloxy and $C_6-C_{10}$ arylsulfonyl;

each m is independently an integer from 1 to 6, and n is an integer from 0 to 3;

which comprises treating a compound of the formula 8

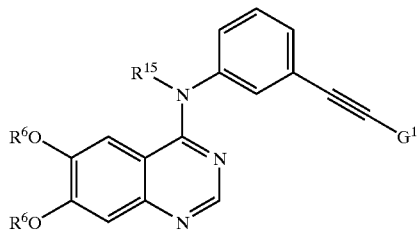

8 wherein $G^1$ is $-C(OH)R^3R^4$, and $R^{15}$, $R^6$, $R^3$ and $R^4$ are as defined above, with a primary or secondary alcohol of the formula $R^7$—OH wherein $R^7$ is as defined above, in the presence of an alkali-metal or alkaline-metal hydroxide, such as sodium hydroxide, lithium hydroxide, cesium hydroxide, calcium hydroxide, magnesium hydroxide or potassium hydroxide, most preferably sodium hydroxide.

In a preferred embodiment of the above reaction, $R^6$ is 2-methoxyethoxy and said alcohol of formula $R^7$—OH is preferably a secondary alcohol.

The present invention also relates to a method of preparing compounds of the formula

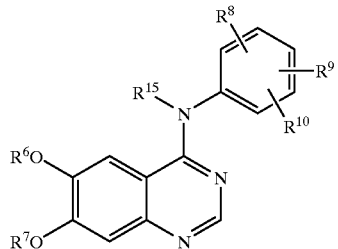

9 and the pharmaceutically acceptable salts and solvates thereof, wherein $R^{15}$, $R^6$ and $R^7$ are as defined above; $R^8$, $R^9$ and $R^{10}$ are each independently selected from H, $C_1-C_{10}$ alkyl, halo, cyano, nitro, trifluoromethyl, difluoromethoxy, trifluoromethoxy, azido, $-OR^{11}$, $-C(O)R^{11}$, $-C(O)OR^{11}$, $-NR^{12}C(O)OR^{14}$, $-OC(O)R^{11}$, $-NR^{12}SO_2R^{14}$, $-SO_2NR^{11}R^{12}$, $-NR^{12}C(O)R^{11}$, $-C(O)NR^{11}R^{12}$, $-NR^{11}R^{12}$, $-S(O)_j(CH_2)_q(C_6-C_{10}$ aryl$)$, $-S(O)_j(C_1-C_6$ alkyl$)$, wherein j is an integer from 0 to 2, $-(CH_2)_q(C_6-C_{10}$ aryl$)$, $-O(CH_2)_q(C_6-C_{10}$ aryl$)$, $-NR^{12}(CH_2)_q(C_6-C_{10}$ aryl$)$, and $-(CH_2)_q(4-10$ membered heterocyclic$)$, wherein q is an integer from 0 to 4; said alkyl group optionally contains 1 or 2 hetero moieties selected from O, $-S(O)_j-$ wherein j is an integer from 0 to 2, and $-N(R^{12})-$ with the proviso that two O atoms, two S atoms, or an O and S atom are not attached directly to each other; said aryl and heterocyclic groups are optionally fused to a $C_6-C_{10}$ aryl group, a $C_5-C_8$ saturated cyclic group, or a 4–10 membered heterocyclic group; and said alkyl, aryl and heterocyclic groups are optionally substituted by 1 to 5 substituents independently selected from halo, cyano, nitro, trifluoromethyl, difluoromethoxy, trifluoromethoxy, azido, $-NR^{12}SO_2R^{14}$, $-SO_2NR^{11}R^{12}$, $-C(O)R^{11}$, $-C(O)OR^{11}$, $-OC(O)R^{11}$, $-NR^{12}C(O)OR^{14}$, $-NR^{12}C(O)R^{11}$, $-C(O)NR^{11}R^{12}$, $-NR^{11}R^{12}$, $-OR^{11}$, $C_1-C_{10}$ alkyl, $-(CH_2)_q(C_6-C_{10}$ aryl$)$, and $-(CH_2)_q(4-10$ membered heterocyclic$)$, wherein q is an integer ranging from 0 to 4;

each $R^{11}$ is independently selected from H, $C_1-C_{10}$ alkyl, $-(CH_2)_q(C_6-C_{10}$ aryl$)$, and $-(CH_2)_q(4-10$ membered heterocyclic$)$, wherein q is an integer ranging from 0 to 4; said alkyl group optionally includes 1 or 2 hetero moieties selected from O, $-S(O)_j-$ wherein j is an integer from 0 to 2, and $-N(R^{12})-$ with the proviso that two O atoms, two S atoms, or an O and S atom are not attached directly to each other; said aryl and heterocyclic $R^{11}$ groups are optionally fused to a $C_6-C_{10}$ aryl group, a $C_5-C_8$ saturated cyclic group, or a 4–10 membered heterocyclic group; and the foregoing $R^{11}$ substituents, except H, are optionally substituted by 1 to 5 substituents independently selected from halo, cyano, nitro, trifluoromethyl, difluoromethoxy, trifluoromethoxy, azido, $-C(O)R^{12}$, $-C(O)OR^{12}$, $-OC(O)R^{12}$, $-NR^{12}C(O)R^{13}$, $-C(O)NR^{12}R^{13}$, $-NR^{12}R^{13}$, hydroxy, $C_1-C_6$ alkyl, and $C_1-C_6$ alkoxy;

each $R^{12}$ and $R^{13}$ is independently H or $C_1$–$C_6$ alkyl; and,
$R^{14}$ is selected from the substituents provided in the definition of $R^{11}$ except $R^{14}$ is not H;

which comprises treating a compound of the formula 10

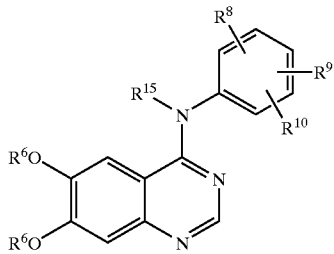

wherein $R^{11}$, $R^6$, $R^8$, $R^9$ and $R^{10}$ are as defined above; with a primary or secondary alcohol of the formula $R^7$—OH wherein $R^7$ is as defined above, preferably a primary alcohol, in the presence of an alkali-metal or alkaline-metal hydroxide, such as sodium hydroxide, lithium hydroxide, cesium hydroxide, calcium hydroxide, magnesium hydroxide or potassium hydroxide, most preferably sodium hydroxide.

The above compounds of formulas 1, 6, 7 and 9 are useful in the treatment of hyperproliferative disorders, such as cancers, in mammals.

The present invention also relates to intermediates of the formula 2 as described above with reference to the preparation of the compounds of formula 1.

The term "halo", as used herein, unless otherwise indicated, includes fluoro, chloro, bromo or iodo. Preferred halo groups are fluoro, chloro and bromo.

The term "alkyl", as used herein, unless otherwise indicated, includes saturated monovalent hydrocarbon radicals having straight, branched or cyclic moieties, or a combination of the foregoing moieties. It is understood that for said alkyl group to include cyclic moieties at least three carbon atoms are required in said alkyl group.

The term "aryl", as used herein, unless otherwise indicated, includes an organic radical derived from an aromatic hydrocarbon by removal of one hydrogen, such as phenyl or naphthyl.

The term "4–10 membered heterocyclic", as used herein, unless otherwise indicated, includes aromatic and non-aromatic heterocyclic groups containing one or more heteroatoms each selected from O, S and N, wherein each heterocyclic group has from 4–10 atoms in its ring system. Non-aromatic heterocyclic groups include groups having only 4 atoms in their ring system, but aromatic heterocyclic groups must have at least 5 atoms in their ring system. The heterocyclic groups include benzo-fused ring systems and ring systems substituted with one or more oxo moieties. An example of a 4 membered heterocyclic group is azetidinyl (derived from azetidine). An example of a 5 membered heterocyclic group is thiazolyl and an example of a 10 membered heterocyclic group is quinolinyl. Examples of non-aromatic heterocyclic groups are pyrrolidinyl, tetrahydrofuranyl, tetrahydrothienyl, tetrahydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups, as derived from the compounds listed above, may be C-attached or N-attached where such is possible. For instance, a group derived from pyrrole may be pyrrol-1-yl (N-attached) or pyrrol-3-yl (C-attached).

The phrase "pharmaceutically acceptable salt(s)", as used herein, unless otherwise indicated, includes salts of acidic or basic groups which may be present in the compounds of the present invention. The compounds prepared according to the present invention that are basic in nature are capable of forming a wide variety of salts with various inorganic and organic acids. The acids that may be used to prepare pharmaceutically acceptable acid addition salts of such basic compounds of are those that form non-toxic acid addition salts, i.e., salts containing pharmacologically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate and pamoate [i.e., 1,1'-methylene-bis-(2-hydroxy-3-naphthoate)] salts. The compounds prepared according to the present invention that include a basic moiety, such as an amino group, may form pharmaceutically acceptable salts with various amino acids, in addition to the acids mentioned above.

Those compounds prepared according to the present invention that are acidic in nature are capable of forming base salts with various pharmacologically acceptable cations. Examples of such salts include the alkali metal or alkaline earth metal salts and, particularly, the calcium, magnesium, sodium and potassium salts of the compounds of the present invention.

The compounds prepared according to the present invention have asymmetric centers and therefore exist in different enantiomeric and diastereomeric forms. This invention relates to all optical isomers and stereoisomers of the compounds prepared according to the present invention, and mixtures thereof. The compounds of formula 1 may also exist as tautomers. This invention relates to the use of all such tautomers and mixtures thereof.

The subject invention also includes isotopically-labelled compounds prepared according to the present invention, and the pharmaceutically acceptable salts thereof, which are identical to those recited in Formula 1, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^2H$, $^3H$, $^{13}C$, $^{14}C$, $^{15}N$, $^{18}O$, $^{17}O$, $^{35}S$, $^{18}F$, and $^{36}Cl$, respectively. Compounds prepared according to the present invention, prodrugs thereof, and pharmaceutically acceptable salts of said compounds or of said prodrugs which contain the aforementioned isotopes and/or other isotopes of other atoms are within the scope of this invention. Certain isotopically-labelled compounds of the present invention, for example those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labelled compounds of Formula 1 of this invention and prodrugs thereof can generally be prepared by carrying out the procedures disclosed in the Schemes and/or in the Examples and Preparations below, by substituting a readily available isotopically labelled reagent for a non-isotopically labelled reagent.

Detailed Description of the Invention
Scheme 1

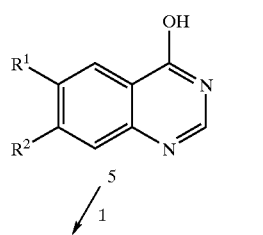

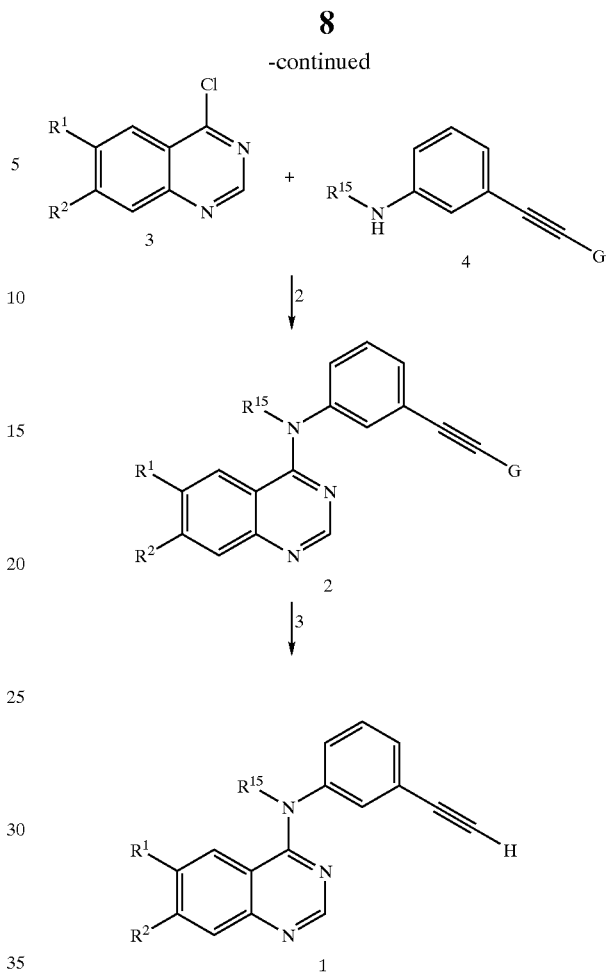

Scheme 2

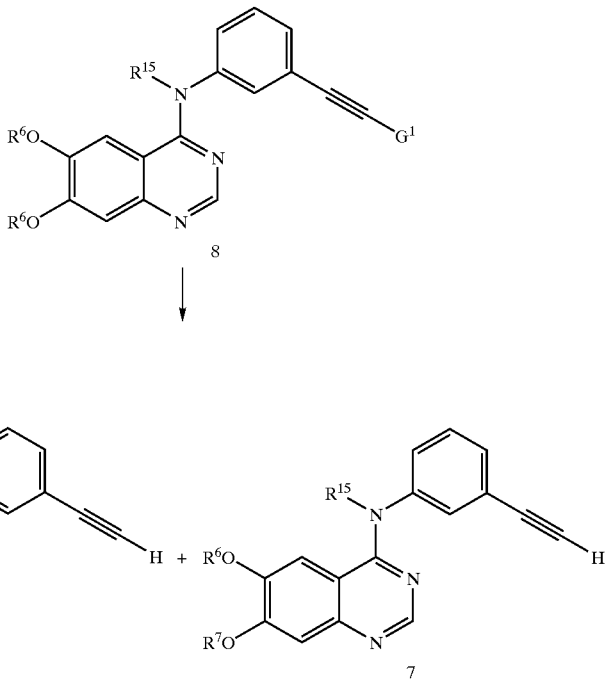

Scheme 3

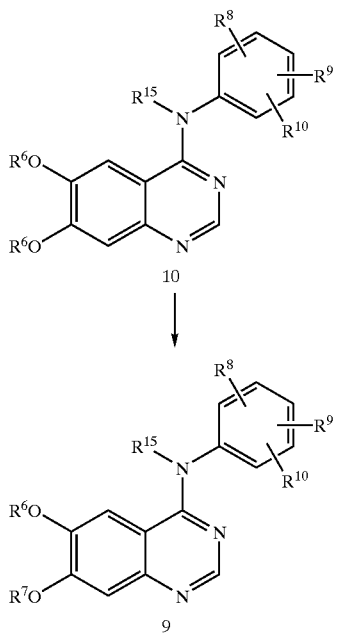

The methods of the present invention may be described through reference to Schemes 1 to 3 above. In the reactions described below, all reactions are conducted at atmospheric pressure and room temperature (about 20–25° C.) unless other conditions are specified. Further, unless otherwise noted, substituents $R^1$–$R^{10}$, $R^{15}$ G and $G^1$ are as described above.

In Scheme 1, compounds of formula 1 may be prepared by first treating starting compound of formula 5, which may be prepared according to methods familiar to those skilled in the art, with thionyl chloride in anhydrous dichloromethane at reflux temperature (about 38–42° C. at atmospheric pressure) to obtain the compound of formula 3. The compound of formula 2 may be obtained by treating the compound of formula 3 with the compound of formula 4 in an organic solvent, such as DMF, DMSO, THF, MeCN, or a mixture of two or more of the foregoing solvents, preferably MeCN, at a temperature ranging from 50° C. to reflux, preferably reflux. The foregoing acronyms are as defined in the Summary of the Invention, referred to above. The compound of formula 1 may be prepared by treating the compound of formula 2 with an alkali-metal or alkaline-metal hydroxide in a solvent comprising $C_1$–$C_{10}$ alkyl substituted by at least one hydroxy group where G is —C(OH)$R^3R^4$, or with a tetra-($C_1$–$C_6$ alkyl)-ammonium fluoride compound in an aprotic solvent where G is —SiR$^3R^4R^5$. Where G is —C(OH)$R^3R^4$, the solvent is preferably a secondary alcohol, such as butan-2-ol or isopropanol, said alkali-metal or alkaline-metal hydroxide may be selected from sodium hydroxide, lithium hydroxide, cesium hydroxide, calcium hydroxide, magnesium hydroxide and potassium hydroxide, preferably sodium hydroxide, and the reaction is preferably run at a temperature ranging from about 100° C. to about 150° C. Where G is —SiR$^3R^4R^5$, the tetra-($C_1$–$C_6$ alkyl)-ammonium fluoride compound is preferably tetra-(n-butyl)-ammonium fluoride, the aprotic solvent may be selected from THF, diethyl ether, DME, toluene, dichloromethane, chloroform, and a mixture of two or more of the foregoing solvents, preferably THF, and the reaction is preferably conducted a temperature ranging from about room temperature to about 70° C. The anti-cancer compounds of formula 1 may be converted to pharmaceutically acceptable salts as described below.

In Scheme 2, anti-cancer compounds of formulas 6 and 7 may be prepared by treating intermediate of formula 8 with a primary or secondary alcohol of formula $R^7$—OH, wherein $R^7$ is as defined above, in the presence of an alkali-metal or alkaline-metal hydroxide such as sodium hydroxide, lithium hydroxide, cesium hydroxide, calcium hydroxide, magnesium hydroxide or potassium hydroxide, preferably sodium hydroxide, at a temperature ranging from about 100° C. to about 150° C. Use of a secondary alcohol of formula $R^7$—OH will minimize conversion to the asymmetric analogue of formula 7, while use of a primary alcohol of formula $R^7$—OH will increase the relative concentration of the asymmetric analogue of formula 7. Thus, depending on the analogue that is preferred, a secondary or primary alcohol may be preferred. The compounds of formula 6 and 7 may be separated by various methods, such as chromatography, which are familiar to those skilled in the art. The compounds of formula 6 and 7 may be converted to pharmaceutically acceptable salts as described below.

In Scheme 3, compounds of formula 9 may be prepared by treating compounds of formula 10 with a primary or secondary alcohol of formula $R^7$—OH as described above in reference to Scheme 2. Since the goal of the reaction of Scheme 3 is the preparation of the asymmetric analogue, the use of primary alcohol of formula $R^7$—OH is preferred. The compounds of formula 9 may be converted to pharmaceutically acceptable salts as described below.

Certain compounds prepared according to the present invention referred to above may have asymmetric carbon atoms. Compounds having a mixture of isomers at one or more centers will exist as diastereomeric mixtures, which can be separated into their individual diastereomers on the basis of their physical chemical differences by methods known to those skilled in the art, for example, by chromatography or fractional crystallization. All such isomers, including diastereomer mixtures, are considered as part of the invention.

The compounds referred to above that are basic in nature are capable of forming a wide variety of different salts with various inorganic and organic acids. Although such salts must be pharmaceutically acceptable for administration to mammals, it is often desirable in practice to initially isolate the compound of the present invention from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the basic compounds of this invention are readily prepared by treating the basic compound with a substantially equivalent amount of the chosen mineral or organic acid in an aqueous solvent medium or in a suitable organic solvent, such as methanol or ethanol. Upon careful evaporation of the solvent, the desired solid salt is readily obtained. The desired acid salt can also be precipitated from a solution of the free base in an organic solvent by adding to the solution an appropriate mineral or organic acid.

Those compounds referred to above that are acidic in nature, are capable of forming base salts with various pharmacologically acceptable cations. Examples of such salts include the alkali metal or alkaline-earth metal salts and particularly, the sodium and potassium salts. These salts are all prepared by conventional techniques. The chemical bases which are used as reagents to prepare the pharmaceutically acceptable base salts of this invention are those which form non-toxic base salts with the acidic compounds of the present invention. Such non-toxic base salts include those derived from such pharmacologically acceptable cations as sodium, potassium, calcium and magnesium, etc. These salts can easily be prepared by treating the corresponding acidic compounds with an aqueous solution containing the desired alkali metal alkoxide or metal hydroxide, and then evaporating the resulting solution to dryness, preferably under reduced pressure. Alternatively, they may also be prepared by mixing lower alkanolic solutions of the acidic compounds and the desired alkali metal alkoxide or metal hydroxide together, and then evaporating the resulting solution to dryness in the same manner as before. In either case, stoichiometric quantities of reagents are preferably employed in order to ensure completeness of reaction and maximum yields of the desired final product.

The Examples provided below further exemplify the methods and intermediates of the present invention, although it is understood that the scope of the present invention is not limited by the following examples.

EXAMPLE 1

Preparation of 3-[(trimethylsilyl)ethynyl] nitrobenzene

A mixture of 1-bromo-3-nitrobenzene (10.0 g, 49.45 mmol) and trimethylsilylacetylene (8.4 mL, 59.34 mmol) was treated with triethylamine (33 mL), giving a small amount of white precipitate. The resultant mixture was treated with dichlorobis(triphenylphonsphone)palladium II (7 mgs, 0.01 mmol) and copper (I) iodide (8.5 mgs, 0.04 mmol) and heated at 80–85° C. (oil bath temperature) for 4 hours. The resultant bright yellow mixture was allowed to cool to room temperature and the solid was removed by filtration with the aid of triethylamine (33 mL). The clear yellow solution was concentrated by evaporation and dried in vacuo at room temperature overnight to give the title product (11.11 g, 102%) as a dark brown oil. gc/mass spectroscopy indicated that the final compound was 100% pure m/e 219 (M+H)$^+$

EXAMPLE 2

Preparation of 3-[-(trimethylsilyl)ethynyl]aniline

A mixture of the nitro compound, 3-[(trimethylsilyl) ethynyl]nitrobenzene, prepared as described above (0.86 g, 3.92 mmol) in 2-propanol (30 mL) was degassed with nitrogen and treated with 5% platinum on alumina (268 mgs). The mixture was shaken under an atmosphere of hydrogen (30 psi) on a Parr shaker apparatus for 22 hours. The reaction mixture was filtered through a short pad of Celite™ (diatamaceous earth) and concentrated by evaporation to give an oil which was dried in vacuo overnight to give the title product (692 mg, 93%) as a yellow brown oil.

$\delta_H$ (300 MHz; CDCl$_3$) 0.24 (9H, s), 3.56 (2H, bs), 6.62 (1H, ddd, J=1.0, 2.3 & 8.0), 6.78 (1H, t, J=2.2), 6.87 (1H, dt, J=7.7 & 1.2), 7.07 (1H, t, J=7.8); d$_c$ (75.5 MHz; CDCl$_3$) 93.4, 105.4, 115.6, 118.2, 122.4, 123.8, 129.2, 146.2; m/e 190 (M+H)$^+$

EXAMPLE 3

Preparation of 6,7-bis(2-methoxyethoxy)-N-[3-[(trimethylsilyl)ethynyl]phenyl]-4-quinazolinamine, monohydrochloride 4-Chloro-6,7-bis(2-methoxyethoxy)quinazoline (942 mg, 3.01 mmol) was treated with a solution of the aniline (645 mgs, 3.41 mmol) in 2-propanol (14 mL) and heated at reflux for 2.5 hours. The mixture was allowed to cool to room temperature and stirred for 1 hour. The solid was collected by filtration, washed with 2-propanol (5 mL) and dried in vacuo overnight to give the title product (1.33 g, 88%) as a white solid.

$\delta_H$(400 MHz; CDCl$_3$) 0.21 (9H, s), 3.38 (3H, s), 3.41 (3H, s), 3.72 (2H, m), 3.77 (2H, m), 4.10 (2H, s), 4.53 (2H, s), 7.20 (1H, t, J=7.8), 7.23–7.28 (2H, m), 7.75 (1H, d, J 7.8), 7.88 (1H, s), 8.20 (1H, s), 8.42 (1H, s); m/e 466 (M+H)$^+$

EXAMPLE 4

Preparation of N-(3-ethynylphenyl)-6,7-bis(2-methoxyethoxy)-4-quinazolinamine, monohydrochloride A slurry of the silyl compound, 6,7-bis(2-methoxyethoxy)-N-[3-[(trimethylsilyl)ethynyl]phenyl]-4-quinazolinamine monohydrochloride, prepared above (1.22 g, 2.43 mmol) in tetrahydrofuran (6.1 mL) was treated with a 1M solution of tetra-n-butylammonium fluoride in tetrahydrofuran (2.6 mL, 2.55 mmol) and stirred at room temperature for 1 hour. The solution was treated with 2-propanol (12.2 mL) and concentrated by evaporation. The oil in 2-propanol (20 mL) was treated with concentrated hydrochloric acid (0.2 mL) giving a precipitate. The mixture was stirred at room temperature for 1 hour. The solid was collected by filtration, washed with 2-propanol (2 mL) and dried in vacuo to afford the title product (747 mg, 72%) as an off white solid (mp 226–229° C.).

$\delta_H$ (300 MHz; d$_6$-DMSO) 3.36 (6H, s), 3.77–3.80 (4H, m), 4.30 (1H, s), 7.39 (1H, s), 7.41 (1H, d, J=7.8), 7.50 (1H, t, J=7.9), 7.79 (1H, d, J=8.1), 7.88 (1H, s), 8.40 (1H, s), 8.86 (1H, s), 11.48 (1H, bs); $\delta_C$ (100 MHz; d$_6$-DMSO) 58.4, 58.5, 68.7, 69.2, 69.7, 67.0, 81.3, 83.0, 100.3, 105.2, 107.2, 121.9, 125.4, 127.6, 128.9, 129.2, 135.2, 137.7, 148.3, 149.2, 155.4, 158.0; m/e 394 (M+H)$^+$

EXAMPLE 5

Preparation of 4-[3-[[6,7-bis(2-methoxyethoxyl-4-quinazolinyl]amino]phenyl]-2-methyl-3-butyn-2-ol, monohydrochloride 4-Chloro-6,7-bis(2-methoxyethoxy)quinazoline (15 g, 48 mmol), 4-(3-aminophenyl)-2-methyl-3-butyn-2-ol (9.2 g, 52.8 mmol) and acetonitrile (225 mL) was heated at reflux for 5 hours. The mixture was cooled to cool to 5–10° C. and stirred for 1 hour. The solid was collected by filtration, washed with acetonitrile (15 mL) and dried in vacuo overnight to give the title product (23.4 g, 100%) as a white solid.

$\delta_H$ (400 MHz; d$_6$-DMSO) 1.44 (6H,s), 3.31–3.32 (6H, m), 3.69–3.75 (4H, m), 4.24–4.30 (2H, m), 4.35–4.37 (2H, m),7.25 (1H, m), 7.39 (2H, m), 7.72–7.74 (2H, m)ijio, 8.47 (1H, s), 8.79 (1H, s), 11.64 (1H, s); m/e 452 (M+H)$^+$

EXAMPLE 6

Preparation of 4-[3-[[6,7-bis(2-methoxyethoxy]-4-quinazolinyl]amino]phenyl]-2-methyl-3-butyn-2-ol 4-[3-[[6,7-Bis(2-methoxyethoxyl-4-quinazolinyl]amino] phenyl]-2-methyl-3-butyn-2-ol, monohydrochloride, prepared above (19.0 g, 39.7 mmol), water (95 mL) and ethyl acetate (380 mL) were stirred together at room temperature to form a mixture. The pH of the mixture was adjusted to pH 10–12 with 50% aqueous sodium hydroxide solution to give two clear layers. The organic layer was separated from the aqueous layer and concentrated under vacuum to a volume of ~190 mL. After a period of granulation in an ice bath crystals of title product were formed, filtered off and dried to yield product (15.13 g, 86%).

$\delta_H$ (400 MHz; CDCl$_3$) 1.56 (6H,s), 3.35 (3H,s), 3.37 (3H, s), 3.7–3.71 (4H, m), 4.13–4.19 (4H, m), 7.0 (1H, m), 7.13–7.17 (2H, m), 7.3 (1H, m), 7.6 (2H, m), 8.55 (1H, s); m/e 452 (M+H)$^+$

EXAMPLE 7

Preparation of N-(3-ethynylphenyl)-6,7-bis(2-methoxyethoxy)-4-quinazolinamine, monohydrochloride 4-[3-[[6,7-Bis(2-methoxyethoxy]-4-quinazolinyl]amino]phenyl]-2-methyl-3-butyn-2-ol, monohydrochloride, prepared as described above (32.34 g, 66.3 mmol), water (300 mL) and butan-1-ol (600 mL) were stirred together at room temperature to form a mixture. The pH of the mixture was adjusted to pH 10–12 with 50% aqueous sodium hydroxide solution to give two clear layers. The organic layer was separated from the aqueous layer and concentrated under atmospheric pressure, so that water was azeotropically removed from the butan-1-ol solution. The final volume of butan-1-ol solution was ~300 mL. Anhydrous solid sodium hydroxide (0.13 g, 3.3 mmol) was added to the azeotropically dried butan-1-ol solution and the resultant mixture was heated under reflux at 115–120° C. for 24 hours. Butan-1-ol (150 mL) was removed by distillation and the concentrated reaction mixture cooled to 15–25° C. Concentrated hydrochloric acid (6.1 mL) and butan-1-ol (60 mL) were added to the cooled concentrate and the mixture was granulated overnight at 20–25° C. to establish crystallization. The title product crystals were isolated by filtration and dried under vacuum at 45–50° C. to remove butan-1-ol. Yield (21.0 g, 73.7%). Purity by HPLC 96.5%.

EXAMPLE 8

Preparation of N-(3-ethynylphenyl)-6,7-bis(2-methoxyethoxy)-4-quinazolinamine, methanesulfonic acid salt 4-[3-[[6,7-Bis(2-methoxyethoxy]-4-quinazolinyl]amino]phenyl]-2-methyl-3-butyn-2-ol, monohydrochloride, prepared above (32.34 g, 66.3 mmol), water (300 mL) and butan-1-ol (600 mL) were stirred together at room temperature to form a mixture. The pH of the mixture was adjusted to pH 10–12 with 50% aqueous sodium hydroxide solution to give two clear layers. The organic layer was separated from the aqueous layer and concentrated under atmospheric pressure, so that water was azeotropically removed from the butan-1-ol solution. The final volume of butan-1-ol solution was ~300 mL. Anhydrous solid sodium hydroxide (0.13 g, 3.3 mmol) was added to the azeotropically dried butan-1-ol solution and the resultant mixture was heated under reflux at 115–120° C. for 24 hours. The reaction mixture was cooled to 15–25° C. and methanesulfonic acid (4.6 mL) was added and the mixture was granulated overnight at 20–25° C. to establish crystallization. The title product crystals were isolated by filtration, washed with butan-1-ol (25 mL) and dried under vacuum at 45–50° C. to remove butan-1-ol. Yield (29.16 g, 90%). Purity by HPLC 96.7%.

EXAMPLE 9

Preparation of N-(3-ethynylphenyl-6,7-bis(2-methoxyethoxy)4-quinazolinamine, monohydrochloride 4-[3-[[6,7-Bis(2-methoxyethoxy]-4-quinazolinyl]amino]phenyl]-2-methyl-3-butyn-2-ol, prepared above (20.0 g, 44.3 mmol), anhydrous solid sodium hydroxide (0.09 g, 2.2 mmol) and butan-2-ol (400 mL) were stirred together and heated under reflux at 100–102° C. for 36 hours. The reaction mixture was cooled to 15–25° C. and concentrated hydrochloric acid (4.1 mL) was added. The resultant mixture was granulated overnight at 20–25° C. to establish crystallization. The title product crystals were isolated by filtration, washed with butan-2-ol (25 mL) and dried under vacuum at 45–50° C. to remove butan-2-ol. Yield (17.7 g, 93%). Purity by HPLC 99.1%.

EXAMPLE 10

Preparation of N-(3-ethynylphenyl)-6,7-bis(2-methoxyethoxy)-4-quinazolinamine, monohydrochloride 4-[3-[[6,7-Bis(2-methoxyethoxy]-4-quinazolinyl]amino]phenyl]-2-methyl-3-butyn-2-ol, prepared above (20.0 g, 44.3 mmol), anhydrous solid sodium hydroxide (260 mg, 6.5 mmol) and propan-2-ol (200 mL) were stirred together and heated in a pressure vessel at 135–140° C. for 23 hours. The reaction mixture was cooled to 60–65° C. and concentrated hydrochloric acid (4.8 mL) was added. The resultant mixture was granulated overnight at 20–25° C. to establish crystallization. The mixture was treated with water (10 mL) and stirred at 58–60° C. for 21 hours, cooled to 15–20° C. and granulated for 2 hours. The title product crystals were isolated by filtration, washed with propan-2-ol (2×30 mL) and dried under vacuum at 45–50° C. to remove propan-2-ol. Yield (17.6 g, 92%).

EXAMPLE 11

Preparation of N-(3-ethynylphenyl)-6,7-bis(2-methoxyethoxy)-4-quinazolinamine, monohydrochloride 4-[3-[[6,7-Bis(2-methoxyethoxy]-4-quinazolinyl]amino]phenyl]-2-methyl-3-butyn-2-ol, prepared above (5.0 g, 11 mmol), anhydrous solid sodium hydroxide (44 mg, 11 mmol) and 2-methoxyethanol (50 mL) were stirred together and heated at reflux for 47 hours. The reaction mixture was cooled to 20–25° C. and concentrated hydrochloric acid (1.1 mL) was added. The resultant mixture was granulated at 20–25° C. for 1 hour to establish crystallization. The title product crystals were isolated by filtration, washed with 2-methoxyethanol (10 mL) and dried under vacuum at 45–50° C. to remove 2-methoxyethanol. Yield (3.73 g, 78%).

EXAMPLE 12

Preparation of N-(3-ethynylphenyl)-6,7-bis(2-methoxyethoxy)-4-quinazolinamine, methanesulfonic acid salt 4-[3-[[6,7-Bis(2-methoxyethoxy]-4-quinazolinyl]amino]phenyl]-2-methyl-3-butyn-2-ol, prepared above (20.0 g, 44.3 mmol), anhydrous solid sodium hydroxide (0.09 g, 2.2 mmol) and butan-2-ol (400 mL) were stirred together and heated under reflux at 100–102° C. for 36 hours. The reaction mixture was cooled to 15–25° C. and methanesulfonic acid (5.1 g, 53.2 mmol) was added. The resultant mixture was granulated overnight at 20–25° C. to establish crystallization. The title product crystals were isolated by filtration, washed with butan-2-ol (25 mL) and dried under vacuum at 45–50° C. to remove butan-2-ol. Yield (19.45 g, 90%). Purity by HPLC 98.5%.

EXAMPLE 13

Preparation of N-(3-ethylphenyl)-6,7-bis(2-methoxyethoxy)-4-quinazolinamine

4-Chloro-6,7-bis(2-methoxyethoxy)quinazoline (50 g, 160 mmol), 3-ethylaniline (21.34 g, 176 mmol) and propan-2-ol (500 mL) was heated at 78–82° C. for 16 hours. The mixture was cooled to cool to 5–10° C. and stirred for 1 hour. The solid was collected by filtration, and mixed with water (200 mL) and ethyl acetate (500 mL). The mixture was adjusted to pH 10–12 with 50% aqueous sodium hydroxide to give to clear layers. The organic layer was separated and washed with water (200 mL), brine (200 mL) and dried over anhydrous magnesium sulfate, filtered and concentrated to an oil. The oil was allowed to solidify and dried under vacuum at 20–25° C. to give the title product (57.2 g, 90%) as a white solid. mp 72–74° C.;

$\delta_H$ (300 MHz; CDCl$_3$) 1.16 (3H, t, J=7.6), 2.58 (2H, q, J=7.6), 3.32 (3H, s), 3.34 (3H, s), 2.01–2.47 (2H, m), 2.08–2.54 (2H, m), 4.07–4.12 (4H, m), 6.91 (1H, d, J=7.6), 7.11 (1H, s), 7.21 (1H, t, J=7.8), 7.35 (1H, s), 7.42 (1H, s), 7.48 (1H, d, J=8.0), 8.13 (1H, bs), 8.58 (1H, s); $\delta_C$ (75.5 MHz; CDCl$_3$) 15.4, 28.8, 59.1, 68.2, 68.9, 70.4, 70.8, 103.0, 108.3, 109.3, 119.7, 121.7, 123.9, 128.8, 138.6, 145.1, 147.0, 148.6, 153.6, 154.4, 156.9; $v_{max}$ (KBr) cm$^{-1}$ 3136 (s), 1624 (s), 1575 (s), 1535 (s), 1487 (s); m/z 398 (M+H)$^+$ (Found: C, 65.64; H, 6.96; N, 10.32. C$_{22}$H$_{27}$N$_3$O$_4$.0.25H$_2$O requires C, 65.73; H, 6.90; N, 10.45%).

EXAMPLE 14

Preparation of N-(3-ethylphenyl)-6-(2-methoxyethoxy)-7-benzyloxy-4-quinazolinamine N-(3-ethylphenyl)-6,7-bis(2-methoxyethoxy)-4-quinazolinamine, prepared as described above (4.0 g, 10 mmol), solid anhydrous sodium hydroxide (104 mg, 2.6 mmol) and benzyl alcohol (20 mL) was heated at 150–152° C. for 23 hours. The reaction mixture was allowed to cool to room temperature and purified by column chromatography on silica gel using a gradient system with ethyl acetate/hexane as eluent to give a white solid which was dried under vacuum at 45–50° C. to give the title product. (2.52 g, 58%), mp 156–157° C.

$\delta_H$ (300 MHz; CDCl$_3$) 1.17 (3H, t, J 7.6), 2.58 (2H, q, J 7.6), 3.33 (3H, s), 3.65–3.68 (2H, m), 4.07–4.11 (2H, m), 5.11 (2H, s), 6.93 (1H, d, J 7.7), 7.18–7.29 (5H, m), 7.35–7.42 (4H, m), 7.50 (1H, d, J 8.0), 8.20 (1H, bs), 8.61 (1H, s); $\delta_C$ (75.5 MHz; CDCl$_3$) 14.2, 15.4, 28.8, 59.2, 69.2, 70.7, 70.8, 103.2, 109.1, 109.4, 119.7, 121.7, 124.0, 127.3, 128.1, 128.5, 128.8, 135.8, 138.6, 145.1, 147.0, 148.9, 153.7, 154.2, 156.9; $v_{max}$ (KBr) cm$^{-1}$ 1625, 1611, 1576; m/z 430 (M+H)$^+$; (Found: C, 71.42; H, 6.50; N, 9.48. C$_{26}$H$_{27}$N$_3$O$_3$ requires C, 72.70; H, 6.34; N, 9.78%).

EXAMPLE 15

Preparation of N-(3-ethylphenyl)-6-(2-methoxyethoxy)-7-butyloxy-4-quinazolinamine N-(3-ethylphenyl)-6,7-bis(2-methoxyethoxy)-4-quinazolinamine, prepared above (4.0 g, 10 mmol), solid anhydrous sodium hydroxide (94 mg, 2.36 mmol) and butan-1-ol (20 mL) was heated at reflux for 12 days. The reaction mixture was allowed to cool to room temperature and purified by column chromatography on silica gel using a gradient system with ethyl acetate/hexane as eluent to give a white solid which was dried under vacuum at 45–50° C. to give the title product. 2.57 g, 65%, mp 90–92° C.

$\delta_H$ (300 MHz; CDCl$_3$) 0.93 (3H, t, J 7.4), 1.19 (3H, t, J 7.6), 1.45 (2H, sextet, J 7.5), 1.79 (2H, pentet, J 6.9), 2.61 (2H, q, J 7.6), 3.39 (3H, s), 3.70–3.74 (2H, m), 4.00 (2H, t, J 6.6), 4.12–4.15 (2H, m), 6.94 (1H, d, J 7.7), 7.15 (1H, s), 7.24 (1H, t, J 7.8), 7.34 (1H, s), 7.44 (1H, s), 7.51 (1H, d, J 8.0), 7.95 (1H, bs), 8.60 (1H, s); $\delta_C$ (75.5 MHz; CDCl$_3$) 13.8, 15.4, 19.2, 28.8, 30.8, 59.3, 68.7, 69.3, 70.9, 103.2, 108.2, 108.9, 119.6, 121.6, 124.0, 128.9, 138.6, 145.2, 147.2, 148.8, 153.6, 154.9, 156.8; $v_{max}$ (KBr) cm$^{-1}$ 1618, 1576, 1519; m/z 396 (M+H)$^+$; (Found: C, 70.90; H, 7.56; N, 10.66. C$_{23}$H$_{29}$N$_3$O$_3$ requires C, 69.85; H, 7.39; N, 10.63%).

EXAMPLE 16

Preparation of N-(4-methoxyphenyl)-6,7-bis(2-methoxyethoxy)-4-quinazolinamine

4-Chloro-6,7-bis(2-methoxyethoxy)quinazoline (25 g, 79.9 mmol), 4-anisidine (9.8 g, 79.9 mmol) and propan-2-ol (250 mL) was heated at 78–82° C. for 16 hours. The mixture was cooled to 5–10° C. and stirred for 1 hour. The solid was collected by filtration, and washed with propan-2-ol (25 mL). The isolated solid was recrystallized from ethanol/water which was dried overnight in a vacuum oven at 40–45° C. The recrystallized solid was mixed with water (100 mL) and ethyl acetate (250 mL). The mixture was adjusted to pH 10–12 with 50% aqueous sodium hydroxide to give to clear layers. The organic layer was separated and washed with water (200 mL), brine (200 mL) and dried over anhydrous magnesium sulfate, filtered and concentrated to give a white solid, that was dried under vacuum at 40–45° C. to give the product. 20.86 g, 65%, mp 186–187° C.

$\delta_H$ (300 MHz; CDCl$_3$) 3.31 (3H, s), 3.35 (3H, s), 3.62–3.65 (2H, m), 3.70–3.72 (2H, m), 3.74 (3H, s), 4.04–4.11 (4H, m), 6.83 (2H, d, J 9.0), 7.09 (1H, s), 7.33 (1H, s), 7.46 (2H, d, J 9.0), 8.12 (1H, bs), 1H, s); $\delta_C$ (75.5 MHz; CDCl$_3$) 55.4, 59.2, 68.2, 69.0, 70.4, 70.8, 103.1, 108.3, 109.1, 114.2, 124.7, 131.4, 146.8, 148.6, 153.7, 154.3, 156.7, 157.3; $v_{max}$ (KBr) cm$^{-1}$ 1619, 1590, 1582, 1511; m/z 400 (M+H)$^+$; (Found: C, 63.30; H, 6.37; N. 10.47. C$_{21}$H$_{25}$N$_3$O$_5$ requires C, 63.42; H, 6.31; N, 10.52%).

EXAMPLE 17

Preparation of N-(4-methoxyphenyl)-6-(2-methoxyethoxy)-7-benzyloxy-4-quinazolinamine N-(4-methoxyphenyl)-6,7-bis(2-methoxyethoxy)-4-quinazolinamine, prepared above (2.0 g, 4.6 mmol), solid anhydrous sodium hydroxide (104 mg, 2.6 mmol) and benzyl alcohol (20 mL) was heated at 145–150° C. for 18 hours. The reaction mixture was allowed to cool to room temperature and purified by column chromatography on silica gel using a gradient system with ethyl acetate/hexane as eluent to give a white solid which was dried under vacuum at 45–50° C. to give the product. 0.915 g, 42%, mp 208–209° C.

$\delta_H$ (300 MHz; CDCl$_3$) 3.34 (3H, s), 3.91 (2H, t, J 4.2), 3.74 (3H, s), 4.10 (2H, bs), 5.13 (2H, s), 6.83 (2H, d, J 8.9), 7.20–7.30 (5H, m), 7.36–7.38 (3H, m), 7.47 (2H, d, J 8.9), 8.10 (1H, bs), 8.54 (1H, s); $\delta_C$ (75.5 MHz; CDCl$_3$) 55.5, 59.3, 69.2, 70.7, 70.9, 103.3, 109.0, 109.1, 114.2, 124.6, 127.3, 128.1, 128.5, 131.3, 135.8, 146.8, 148.8, 153.7, 154.2, 154.2, 156.8, 157.2; $v_{max}$ (KBr) cm$^{-1}$ 1619, 1580, 1511; m/z 432 (M+H)$^+$; (Found: C, 69.48; H, 5.85; N, 9.68. C$_{25}$H$_{25}$N$_3$O$_4$ requires C, 69.59; H, 5.84; N, 9.74%).

EXAMPLE 18

Preparation of N-phenyl-N-methyl-6,7-bis(2-methoxyethoxy)-4-quinazolinamine

4-Chloro-6,7-bis(2-methoxyethoxy)quinazoline (10 g, 31.97 mmol), N-methylaniline (3.5 mL, 31.97 mmol) and acetonitrile (100 mL) was heated at 78–82° C. for 24 hours. The mixture was cooled to cool to 5–10° C. and stirred for 0.5 hour. The solid was collected by filtration, and was dried for 5 hours in a vacuum oven at 50–55° C. The isolated solid was mixed with water (50 mL) and ethyl acetate (200 mL). The mixture was adjusted to pH 10–12 with 50% aqueous sodium hydroxide to give to clear layers. The organic layer was separated and washed with water (50 mL), brine (50 mL) and dried over anhydrous magnesium sulfate, filtered and concentrated to give a white solid, that was dried under vacuum at 50–55° C. to give the product. 8.55 g, 70%, mp 109–111° C.

$\delta_H$ (300 MHz; CDCl$_3$) 3.33 (3H, s), 3.39 (3H, s), 3.42–3.45 (2H, m), 3.48–3.51 (2H, m), 3.58 (3H, s), 3.74–3.78 (2H, m), 4.16–4.20 (2H, m), 6.33 (1H, s), 7.11–7.20 (4H, m), 7.83 (2H, t, J 7.8), 8.68 (1H, s); $\delta_C$ (75.5 MHz; CDCl$_3$) 42.0, 59.2, 59.3, 67.6, 68.2, 70.3, 70.4, 106.5, 107.9, 110.9, 125.8, 126.0, 129.9, 147.0, 148.4, 148.7, 153.0, 153.4, 160.4; $\nu_{max}$ (KBr) cm$^{-1}$ 1615, 1571, 1497; m/z 384 (M+H)$^+$; (Found: C, 65.85; H, 6.52; N, 11.01. C$_{21}$H$_{25}$N$_3$O$_4$ requires C, 65.78; H, 6.57; N, 10.96%).

EXAMPLE 19

Preparation of N-phenyl-N-methyl-6-(2-methoxyethoxy)-7-butyloxy-4-quinazolinamine N-Methyl-N-phenyl-6,7-bis(2-methoxyethoxy)-4-quinazolinamine, prepared as described above (1.0 g, 2.61 mmol), solid anhydrous sodium hydroxide (97.5 mg, 2.43 mmol) and butan-1-ol (10 mL) was heated at reflux for 24 hours. The reaction mixture was allowed to cool to room temperature and purified by column chromatography on silica gel using a gradient system with ethyl acetate/hexane as eluent to give a white solid which was dried under vacuum at 45–50° C. to give the product. 517 mg, 52%, mp 62–63° C.

$\delta_H$ (300 MHz; CDCl$_3$) 0.93 (3H, t, J 7.4), 1.45 (2H, sextet, J 7.4), 1.80 (2H, penter, J 6.7), 3.35 (3H, s), 3.44–3.52 (4H, m), 3.59 (3H, s), 4.05 (2H, t, J 6.7), 6.43 (1H, s), 7.12–7.21 (4H, m), 7.34 (2H, t, J 7.7), 8.69 (1H, s); $\delta_C$ (75.5 MHz; CDCl$_3$) 13.8, 19.2, 30.7, 42.0, 59.2, 67.8, 68.6, 70.4, 106.5, 107.7, 110.6, 125.8, 125.9, 129.9, 147.0, 148.6, 153.0, 153.8, 160.4; $\nu_{max}$ (KBr) cm$^{-1}$ 1616, 1572, 1543; m/z 382 (M+H)$^+$; (Found: C, 69.39; H, 7.38; N, 10.86. C$_{22}$H$_{27}$N$_3$O$_3$ requires C, 69.27; H, 7.14; N, 11.02%).

What is claimed is:

1. A method of preparing a compound of formula 1

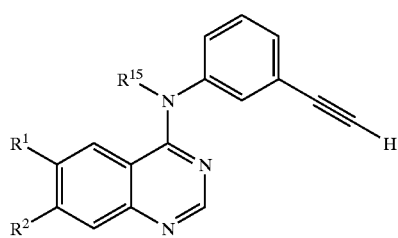

1 or a pharmaceutically acceptable salt or solvate of said compound, wherein:

$R^1$ and $R^2$ are each independently selected from $C_1$–$C_{10}$ alkyl and $C_1$–$C_{10}$ alkoxy wherein said alkyl and alkoxy are optionally substituted by up to 2 substituents independently selected from hydroxy and $C_1$–$C_6$ alkoxy;

$R^{15}$ is H, $C_1$–$C_{10}$ alkyl, or —(CH$_2$)$_q$(C$_6$–$C_{10}$ aryl), wherein q is an integer from 0 to 4;

which comprises treating a compound of formula 2

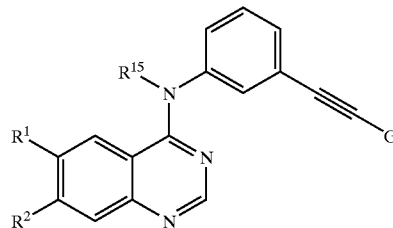

2 wherein $R^{15}$, $R^1$ and $R^2$ are as defined above, and G is a blocking group selected from —C(OH)R$^3$R$^4$ and —SiR$^3$R$^4$R$^5$;

$R^3$, $R^4$ and $R^5$ are each independently $C_1$–$C_6$ alkyl;

with either (a) an alkali-metal or alkaline-metal hydroxide in a solvent comprising hydroxy-substituted $C_1$–$C_{10}$ alkyl where G is —C(OH)R$^3$R$^4$, or (b) a tetra-($C_1$–$C_6$ alkyl)-ammonium fluoride compound in an aprotic solvent where G is —SiR$^3$R$^4$R$^5$.

2. The method of claim 1 wherein G is —C(OH)R$^3$R$^4$, said solvent is a secondary alcohol, and said alkali-metal or alkaline-metal hydroxide is selected from sodium hydroxide, lithium hydroxide, cesium hydroxide, calcium hydroxide, magnesium hydroxide and potassium hydroxide.

3. The method of claim 2 wherein said solvent is butan-2-ol or isopropanol, or a mixture of the two solvents, and said alkali-metal or alkaline-metal hydroxide is sodium hydroxide.

4. The method of claim 1 wherein G is —SiR$^3$R$^4$R$^5$, said tetra-($C_1$–$C_6$ alkyl)-ammonium fluoride compound is tetra-(n-butyl)-ammonium fluoride and said aprotic solvent is selected from tetrahydrofuran, diethyl ether, dimethoxyethane, toluene, dichloromethane, chloroform, and a mixture of two or more of the foregoing solvents.

5. The method of claim 1 wherein both $R^1$ and $R^2$ are 2-methoxyethoxy and $R^{15}$ is H.

6. The method of claim 1 wherein said compound of formula 2 is prepared by treating a compound of the formula 3

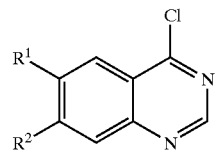

3 wherein $R^1$ and $R^2$ are as defined in claim 1, with a compound of the formula 4

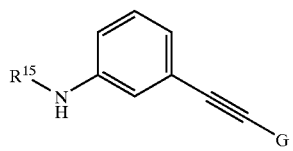

4 wherein $R^{15}$ and G are as defined in claim 1 and wherein the compound of formula 3 is treated with the compound of formula 4 in an organic solvent.

7. The method of claim 6, wherein the organic solvent is selected from dimethylformamide, dimethylsulfoxide, tetrahydrofuran, acetonitrile, and a mixture of two or more of the foregoing solvents.

8. The method of claim 7 wherein said solvent is acetonitrile, both $R^1$ and $R^2$ are 2-methoxyethoxy, and $R^{15}$ is H.

9. The method of claim 6 wherein the compound of formula 3 is prepared by treating a compound of formula 5

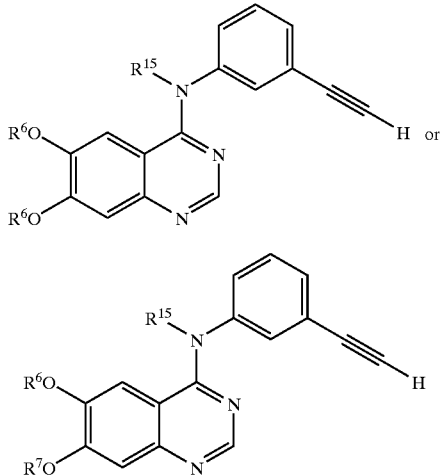

with thionyl chloride in anhydrous dichloromethane.

10. The method of claim 9 wherein $R^1$ and $R^2$ are both 2-methoxyethoxy.

11. A method of preparing a compound of formula 6 or 7

6

7

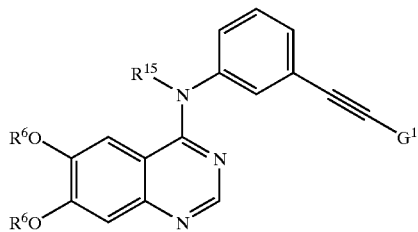

wherein $R^6$ and $R^{15}$ are as defined above, $G^1$ is —C(OH)$R^3R^4$, and $R^3$ and $R^4$ are each independently $C_1$–$C_6$ alkyl;

or a pharmaceutically acceptable salt or solvate thereof, wherein $R^6$ is $C_1$–$C_{10}$ alkyl or —(CH$_2$)$_m$O(CH$_2$)$_n$CH$_3$;

$R^7$ is $C_1$–$C_{10}$ alkyl or —(C$_1$–C$_6$ alkyl)(C$_6$–C$_{10}$ aryl) wherein the foregoing $R^7$ groups are optionally substituted by 1 to 3 substituents independently selected from halo, nitro, trifluoromethyl, trifluoromethoxy, (C$_1$–C$_6$ alkyl)sulfonyl, C$_1$–C$_6$ alkyl, C$_1$–C$_6$ alkoxy, C$_6$–C$_{10}$ aryloxy and C$_6$–C$_{10}$ arylsulfonyl;

each m is independently an integer from 1 to 6, and n is an integer from 0 to 3;

$R^{15}$ is H, $C_1$–$C_{10}$ alkyl, or —(CH$_2$)$_q$(C$_6$–C$_{10}$ aryl), wherein q is an integer from 0 to 4;

which comprises treating a compound of the formula 8

8 with a primary or secondary alcohol of the formula $R^7$—OH wherein $R^7$ is $C_1$–$C_{10}$ alkyl or —(C$_1$–C$_6$ alkyl)(C$_6$–C$_{10}$ aryl) and the foregoing $R^7$ groups are optionally substituted by 1 to 3 substituents independently selected from halo, nitro, trifluoromethyl, trifluoromethoxy, (C$_1$–C$_6$ alkyl)sulfonyl, C$_1$–C$_6$ alkyl, C$_1$–C$_6$ alkoxy, C$_6$–C$_{10}$ aryloxy and C$_6$–C$_{10}$ arylsulfonyl;

in the presence of an alkali-metal or alkaline-metal hydroxide.

12. The method of claim 11 wherein said alkali-metal or alkaline-metal hydroxide is selected from sodium hydroxide, lithium hydroxide, cesium hydroxide, calcium hydroxide, magnesium hydroxide and potassium hydroxide.

13. The method of claim 12 wherein said alkali-metal or alkaline-metal hydroxide is sodium hydroxide, $R^6$ is 2-methoxyethoxy, $R^{15}$ is H, and said alcohol of formula $R^7$—OH is a secondary alcohol.

14. A method of preparing a compound of the formula 9

9

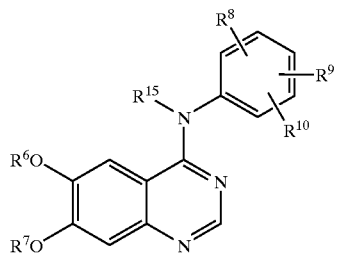

or a pharmaceutically acceptable salt or solvate thereof, wherein $R^6$ is $C_1$–$C_{10}$ alkyl or —(CH$_2$)$_m$O(CH$_2$)$_n$CH$_3$;

$R^7$ is $C_1$–$C_{10}$ alkyl or —(C$_1$–C$_6$ alkyl)(C$_6$–C$_{10}$ aryl) wherein the foregoing $R^7$ groups are optionally substituted by 1 to 3 substituents independently selected from halo, nitro, trifluoromethyl, trifluoromethoxy, (C$_1$–C$_6$ alkyl)sulfonyl, C$_1$–C$_6$ alkyl, C$_1$–C$_6$ alkoxy, C$_6$–C$_{10}$ aryloxy and C$_6$–C$_{10}$arylsulfonyl;

each m is independently an integer from 1 to 6, and n is an integer from 0 to 3;

$R^8$, $R^9$ and $R^{10}$ are each independently selected from H, $C_1$–$C_{10}$ alkyl, halo, cyano, nitro, trifluoromethyl, difluoromethoxy, trifluoromethoxy, azido, —OR$^{11}$, —C(O)R$^{11}$, —C(O)OR$^{11}$, —NR$^{12}$C(O)OR$^{14}$, —OC(O)R$^{11}$, —NR$^{12}$SO$_2$R$^{14}$, —SO$_2$NR$^{11}$R$^{12}$, —NR$^{12}$C(O)R$^{11}$, —C(O)NR$^{11}$R$^{12}$, —NR$^{11}$R$^{12}$, —S(O)$_j$(CH$_2$)$_q$(C$_6$–C$_{10}$ aryl), —S(O)$_j$(C$_1$–C$_6$ alkyl), wherein j is an integer from 0 to 2, —(CH$_2$)$_q$(C$_6$–C$_{10}$ aryl), —O(CH$_2$)$_q$(C$_6$–C$_{10}$ aryl), —NR$^{12}$(CH$_2$)$_q$(C$_6$–C$_{10}$ aryl), and —(CH$_2$)$_q$(4–10 membered heterocyclic), wherein q is an integer from 0 to 4; said alkyl group optionally contains 1 or 2 hetero moieties selected from O, —S(O)$_j$— wherein j is an integer from 0 to 2, and —N(R$^{12}$)— with the proviso that two O atoms, two S atoms, or an O and S atom are not attached directly to each other; said aryl and heterocyclic groups are optionally fused to a C$_6$–C$_{10}$ aryl group, a C$_5$–C$_8$ saturated cyclic group, or a 4–10 membered heterocyclic group; and said alkyl, aryl and heterocyclic groups are optionally substituted by 1 to 5 substituents independently selected from halo, cyano, nitro, trifluoromethyl, difluoromethoxy, trifluoromethoxy, azido, —NR$^{12}$SO$_2$R$^{14}$, —SO$_2$NR$^{11}$R$^{12}$, —C(O)R$^{11}$, —C(O)OR$^{11}$, —OC(O)R$^{11}$, —NR$^{12}$C(O)OR$^{14}$, —NR$^{12}$C(O)R$^{11}$, —C(O)NR$^{11}$R$^{12}$, —NR$^{11}$R$^{12}$, —OR$^{11}$, C$_1$–C$_{10}$ alkyl, —(CH$_2$)$_q$(C$_6$–C$_{10}$ aryl), and —(CH$_2$)$_q$(4–10 membered heterocyclic), wherein q is an integer ranging from 0 to 4;

each R$^{11}$ is independently selected from H, C$_1$–C$_{10}$ alkyl, —(CH$_2$)$_q$(C$_6$–C$_{10}$ aryl), and —(CH$_2$)$_q$(4–10 membered heterocyclic), wherein q is an integer ranging from 0 to 4; said alkyl group optionally includes 1 or 2 hetero moieties selected from O, —S(O)$_j$— wherein j is an integer from 0 to 2, and —N(R$^{12}$)— with the proviso that two O atoms, two S atoms, or an O and S atom are not attached directly to each other; said aryl and heterocyclic R$^{11}$ groups are optionally fused to a C$_6$–C$_{10}$ aryl group, a C$_5$–C$_8$ saturated cyclic group, or a 4–10 membered heterocyclic group; and the foregoing R$^{11}$ substituents, except H, are optionally substituted by 1 to 5 substituents independently selected from halo, cyano, nitro, trifluoromethyl, difluoromethoxy, trifluoromethoxy, azido, —C(O)R$^{12}$, —C(O)OR$^{12}$, —OC(O)R$^{12}$, —NR$^{12}$C(O)R$^{13}$, —C(O)NR$^{12}$R$^{13}$, —NR$^{12}$R$^{13}$, hydroxy, C$_1$–C$_6$ alkyl, and C$_1$–C$_6$ alkoxy;

each R$^{12}$ and R$^{13}$ is independently H or C$_1$–C$_6$ alkyl;

R$^{14}$ is selected from the substituents provided in the definition of R$^{11}$ except H;

R$^{15}$ is H, C$_1$–C$_{10}$ alkyl, or —(CH$_2$)$_q$(C$_6$–C$_{10}$ aryl), wherein q is an integer from 0 to 4;

which comprises treating a compound of the formula 10

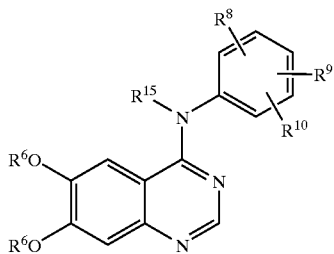

10 wherein R$^{15}$, R$^6$, R$^8$, R$^9$ and R$^{10}$ are as defined above; with a primary or secondary alcohol of the formula R$^7$—OH wherein R$^7$ is C$_1$–C$_{10}$ alkyl or —(C$_1$–C$_6$ alkyl)(C$_6$–C$_{10}$ aryl) and the foregoing R$^7$ groups are optionally substituted by 1 to 3 substituents independently selected from halo, nitro, trifluoromethyl, trifluoromethoxy, (C$_1$–C$_6$ alkyl)sulfonyl, C$_1$–C$_6$ alkyl, C$_1$–C$_6$ alkoxy, C$_6$–C$_{10}$ aryloxy and C$_6$–C$_{10}$arylsulfonyl;

in the presence of an alkali-metal or alkaline-metal hydroxide.

15. The method of claim 14 wherein said alkali-metal or alkaline-metal hydroxide is selected from sodium hydroxide, lithium hydroxide, cesium hydroxide, calcium hydroxide, magnesium hydroxide and potassium hydroxide.

16. The method of claim 15 wherein said alkali-metal or alkaline-metal hydroxide is sodium hydroxide, and said alcohol of formula R$^7$—OH is a primary alcohol.

17. A compound of formula 2

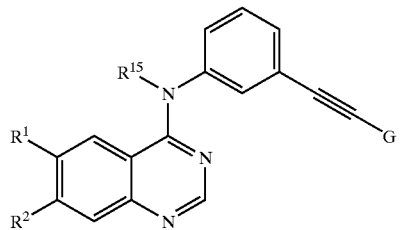

2 wherein R$^1$ and R$^2$ are each independently selected from C$_1$–C$_{10}$ alkyl and C$_1$–C$_{10}$ alkoxy wherein said alkyl and alkoxy are optionally substituted by up to 2 substituents independently selected from hydroxy and C$_1$–C$_6$ alkoxy;

G is a blocking group selected from —C(OH)R$^3$R$^4$ and —SiR$^3$R$^4$R$^5$;

R$^3$, R$^4$ and R$^5$ are each independently C$_1$–C$_6$ alkyl; and,

R$^{15}$ is H, C$_1$–C$_{10}$ alkyl, or —(CH$_2$)$_q$(C$_6$–C$_{10}$ aryl), wherein q is an integer from 0 to 4.

* * * * *